United States Patent
Zhuiykov et al.

[19]

[11] Patent Number: 6,093,295
[45] Date of Patent: Jul. 25, 2000

[54] GAS SENSOR

[75] Inventors: Serge Zhuiykov, Eaglehawk; Alan Walker, Kangaroo Flat; Harold S. Kanost, Eaglehawk, all of Australia

[73] Assignee: Ceramic Oxide Fabricators Pty Ltd, Victoria, Australia

[21] Appl. No.: 08/913,266
[22] PCT Filed: Mar. 8, 1996
[86] PCT No.: PCT/AU96/00132
§ 371 Date: Sep. 10, 1997
§ 102(e) Date: Sep. 10, 1997
[87] PCT Pub. No.: WO96/28724
PCT Pub. Date: Sep. 19, 1996

[30] Foreign Application Priority Data

Mar. 10, 1995 [AU] Australia ............... PN 1666

[51] Int. Cl.⁷ ............... G01N 27/407
[52] U.S. Cl. ........... 204/427; 204/412; 204/426
[58] Field of Search ............ 204/421–429

[56] References Cited
U.S. PATENT DOCUMENTS

| | | | |
|---|---|---|---|
| 3,468,780 | 9/1969 | Fischer ................... | 204/422 |
| 3,597,345 | 8/1971 | Hickam et al. ........... | 204/427 |
| 4,132,615 | 1/1979 | Linder et al. ............. | 204/428 |
| 4,189,355 | 2/1980 | Fujishiro et al. ......... | 204/426 |
| 4,212,273 | 7/1980 | Maruoka ................. | 204/428 |

Primary Examiner—T. Tung
Attorney, Agent, or Firm—Fulbright & Jaworski, L.L.P.

[57] ABSTRACT

A sensor for measuring the oxygen and/or unburnt fuel content of a combustion gas includes an outer tube (20) sealed at one end by a pellet (17) of oxygen sensitive solid electrolyte. Solid electrolyte (17) has an electrode (21) formed on the outer side thereof. The sensor also includes an inner tube (13) that is sealed by a disc (14) of solid electrolyte. Disc (14) has electrodes (15, 16) formed on the inner and outer surfaces thereof. The internal side of solid electrolyte (17) is electrically connected to electrode (16). Outer tube (20) is provided with apertures (24) and the annular space between outer tube (20) and inner tube (13) is coated with a platinum catalyst (18). In use, combustion gas contacts outer electrode (21). Combustion gas passes through apertures (24) and along the annular space. During passage of combustion gas through the annular space, the combustion gas comes into close proximity with the oxidation catalyst (18) and the oxidation catalyst (18) acts to equilibrate the combustion gas. Equilibrated combustion gas therefore comes into contact with electrode (16). A reference gas of known oxygen content is passed along bore (5) of an innermost tube (1) and the reference gas comes into contact with electrode (15). Electrical connectors are used to measure the Nernst emf established between the electrodes. The measured emf allows the oxygen content and/or the unburnt fuel content of the combustion gas to be determined. In another embodiment, solid electrolyte (17) has another electrode formed on the inner surface thereof and equilibrated combustion gas contacts that electrode and also electrode (16).

4 Claims, 4 Drawing Sheets

GAS SENSOR

BACKGROUND OF THE INVENTION

1. Field of the Invention

The present invention relates to a sensor used in combustion gas streams. In one embodiment, the sensor may be used to determine if non-equilibrium conditions or incomplete combustion are present. In another embodiment, the sensor may be used to determine the concentration of oxygen and/or unburnt fuel in the combustion gas stream.

2. Description of the Related Technology

Combustion of fossil fuels and hydrocarbon fuels is a widely used method for obtaining energy in a large number of industries. Complete combustion of hydrocarbon fuels converts the hydrocarbons in the fuel into carbon dioxide and water, in accordance with the reaction given in equation ①;

$$C_xH_y+(x+y/4)O_2 \rightarrow xCO_2+y/2H_2O \qquad (1)$$

In practice, there will also occur other incomplete combustion reactions, for example:

$$C_xH_y+(x/2)O_2 \rightarrow xCO+y/2H_2 \qquad (2)$$

Incomplete combustion can occur if there is excess fuel. It can also occur with excess oxygen, if the fuel and air are not sufficiently well mixed.

Throughout this specification, the expression "combustion gas" is taken to mean off-gas, flue gas or exhaust gas from a combustion process. The combustion process may be the burning of any fossil-fuel or hydrocarbon fuel, and includes the burning of solid fuels, such as coal, for example as used in furnaces, kilns, boilers and the like, and the burning of liquid fuels, such as fuel oil and other petroleum products.

Sensors for measuring the oxygen content of combustion gases, such as engine exhaust gases and furnace off gases, have been described in the prior art. Such sensors generally utilise oxygen ion-conducting solid electrolytes. When opposed faces of the solid electrolyte are exposed to different oxygen partial pressures, an emf (E), or electrical potential difference, is developed which obeys the Nernst equation:

$$E = \frac{RT}{4F} \ln \frac{(pO_2)\ \text{inside}}{(pO_2)\ \text{outside}}$$

where:

T is temperature (Kelvin)

R is the gas constant

F is Faradays constant ln is the mathematical symbol for natural logarithm ($pO_2$) inside is the oxygen partial pressure at the inside face of the electrolyte, and ($pO_2$) outside is the oxygen partial pressure at the outside face of the electrolyte.

Known sensors utilise electrodes formed at the surfaces of the solid electrolyte and measurement of the electrical potential difference (also commonly referred to as 'emf' or 'voltage') between the electrodes enables a measurement of the difference between the oxygen partial pressures in the gas streams contacting the electrodes. If a reference gas of known oxygen concentration is used to contact one electrode, the oxygen concentration of a test gas or a combustion gas contacting the other electrode can be determined.

One sensor of known design includes a hollow tube made of a refractory material, such as alumina, and having a disc plug or pellet of solid electrolyte sealed in one end of the tube. Other sensors utilise a tube made entirely of the solid electrolyte. Australian Patent No. 466,251 in the name of Commonwealth Scientific and Industrial Research Organisation, describes various forms of oxygen sensors and the entire contents of this patent are incorporated herein by reference.

Many solid electrolyte materials are known to be suitable for use in oxygen sensors. Examples include zirconia or hafnia, both fully stabilised or partially stabilised by doping with calcia, magnesia, yttria, scandia or one or a number of rare earth oxides and thoria, also doped with calcia, yttria or a suitable rare earth oxide. Australian Patent No. 513,552 discloses the addition of alumina to these solid electrolyte materials to produce a composite solid electrolyte which is particularly suitable for sealing into the end of an alumina tube, thereby making a rugged and leak-tight sensor useful for demanding industrial applications. Australian Patent Application No. 47828/78 disclose the use of magnesium aluminate spinel as an alternative to alumina, either for the supporting tube or as the inert diluent in the composite solid electrolyte material.

The electrodes on solid electrolyte oxygen sensors generally consist of porous coatings of noble metals such as platinum, gold, palladium or silver, or alloys of these elements. For measurements in gases using a gaseous reference an electrode is required on each surface of the solid electrolyte; for measurements in molten metals an electrode is required only on the reference side of the solid electrolyte, and then only if a gaseous reference is used. If a solid reference, e.g., a metal/metal oxide mixture, is used there is no need for a separate noble metal electrode; the solid reference mixture serves as the electrode.

The above described sensors can be used to assist in controlling the fuel/air ratio in combustion processes for efficient fuel use. However, in some instances, the combustion process may not be complete at the point of measurement, so that there may be unused oxygen, unburnt fuel and other products of incomplete combustion present. In this case, the sensors described above may give an accurate but misleading measurement of oxygen concentration, showing what may appear to be excess oxygen but which in fact is oxygen that has not yet been consumed.

It is an object of the present invention to provide a sensor that can detect the presence of non-equilibrium or incomplete combustion in a combustion gas.

In a first aspect, the present invention provides a sensor for detecting non-equilibrium conditions in a combustion gas comprising a solid electrolyte having a first electrode in electrical contact with a first part of the solid electrolyte and a second electrode in electrical contact with a second part of the solid electrolyte, the second part being on an opposite side of the solid electrolyte to the first part, and gas pathway means along which a combustion gas must pass to reach the second electrode, said gas pathway means arranged such that combustion gas passes or contacts an oxidation catalyst before reaching the second electrode.

In use of the sensor of the first aspect of the present invention, the sensor is placed in a combustion gas stream and combustion gas contacts the first electrode. The combustion gas that travels along the gas pathway means must contact the oxidation catalyst before reaching the second electrode. The oxidation catalyst is effective to catalyse the reaction of any unburnt combustible gas with oxygen to form carbon dioxide, and this ensures that the combustion gas that contacts the second electrode has reached equilibrium and that combustion is essentially complete. Oxidation in the presence of the catalyst, also known as "equilibration", consumes excess oxygen present in the combustion gas and accordingly, if the combustion gas stream is not in equilibrium, the second electrode will be exposed to a gas having a lower oxygen partial pressure than the gas stream contacting the first electrode. This will result in an electrical potential difference being produced. Measurement of a potential difference will indicate that the combustion gas stream is not in equilibrium. If, however, the combustion gas stream is in equilibrium, the catalyst in the gas pathway means will not catalyse any oxidation reactions and, the oxygen partial pressure of the gas contacting the second electrode will be the same as the gas contacting the first electrode. In this case, no electrical potential difference will arise.

In a preferred embodiment of the first aspect of the invention, the sensor includes an elongate tube having the solid electrolyte located at and closing one end thereof. The first and second electrodes are located on either of the inner and outer faces of the solid electrolyte, with 'inner and outer faces' referring to those faces at the interior and exterior regions of the tube, respectively. Preferably, the first electrode is located on the outer face of the solid electrolyte and the second electrode is located on the inner face of the solid electrolyte. The elongate tube includes one or more apertures therein and, in use, the combustion gas can pass through the one or more apertures and pass along the inside of the elongate tube to contact the second electrode. In this case, the gas pathway means comprises the one or more apertures and an inner bore of the elongate tube. The inner bore of the elongate tube may be coated with an oxidation catalyst or may have an oxidation catalyst arranged therein such that combustion gas entering through the apertures must pass the catalyst or contact the catalyst before reaching the second electrode.

In another embodiment, the elongate tube has an inner rod or tube mounted therein with an annular space being defined between an inner wall of the elongate tube and an outer wall of the inner rod or tube. This annular space defines the gas flow pathway means. The catalyst may comprise a coating of catalyst on the outer wall of the inner rod or tube and/or a coating of catalyst on the inner wall of the elongate tube.

The sensor of the first aspect of the invention should also be provided with means for measuring an electrical potential difference between the first and second electrodes. For example, each electrode may be provided with electrical connections that lead from the respective electrodes and are adapted to be connected to a suitable measuring apparatus. The electrical connectors may comprise conductive paths formed by painting metallic pastes onto the elongate tube and/or the inner rod or tube. Alternatively, the electrical connectors may be one or more wires in electrical contact with each electrode. The skilled addressee will be aware of many arrangements for the electrical connectors that fall within the scope of the present invention and these will not need to be described in greater detail.

The oxidation catalyst may be any catalyst that is capable of catalysing complete combustion. Platinum is the preferred catalyst, although a range of other catalysts, including those used to catalyse automotive exhausts, may also be used.

The electrodes may be of any type suitable for use with solid electrolyte sensors. The electrodes are preferably porous platinum electrodes. The skilled person will recognise that there are many electrodes that will perform satisfactorily and the present invention extends to cover all such electrodes. Electrodes used in solid electrolyte sensors are well known to the skilled addressee and will not be described in greater detail.

In one preferred embodiment of the first aspect of the present invention, the solid electrolyte is described as being located at and closing one end of the elongate tube. This may be achieved by providing a hollow tube, for example of a ceramic or refractory material, and placing a disc, plug or pellet in the end thereof. Alternatively, the elongate tube may be formed from the solid electrolyte and the tube may be made with a closed end.

In another embodiment, the elongate tube may be an open tube and the second electrode located away from the open end and any apertures through which combustion gas may pass. Gas travelling along the tube to the second electrode will still contact the catalyst and this will ensure that the combustion gas has been catalysed and reached equilibrium when it contacts the second electrode.

The present invention also provides a method for detecting non-equilibrium conditions in a combustion gas comprising providing a sensor comprising a solid electrolyte having a first electrode in electrical contact with a first part of the solid electrolyte and a second electrode in electrical contact with a second part of the solid electrolyte, the second part being on an opposite side of the solid electrolyte to the first part, and gas pathway means along which a combustion gas must pass to reach the second electrode, said gas pathway means arranged such that combustion gas passing along said gas pathway means passes or contacts an oxidation catalyst before reaching the second electrode, placing said sensor in a combustion gas stream whereby combustion gas contacts said first electrode and combustion gas passes along said gas pathway means wherein any oxidisable species in said combustion gas are oxidised by the catalyst prior to contacting the second electrode and measuring an electrical potential difference between the first and second electrodes.

In a second aspect, the present invention provides a sensor for measuring oxygen and/or unburnt fuel content of a combustion gas, said sensor including     a first electrode which, in use, is contacted by the combustion gas     a second electrode     a third electrode,     each of said first, second and third electrodes being separated from another of said electrodes by solid electrolyte     a first gas pathway means for passing a reference gas of known oxygen concentration to the third electrode     a second gas pathway means for passing a combustion gas to the second electrode, the second gas pathway means including an oxidation catalyst arranged such that the combustion gas passing along the second gas pathway means must contact or pass in close proximity to the oxidation catalyst, and     means for measuring an electrical potential difference between at least two of the following:
        a) the first and second electrodes;
        b) the first and third electrodes, and
        c) the second and third electrodes.

Throughout this specification, the term "unburnt fuel" is used to denote the products of incomplete combustion, including raw fuel and carbon monoxide.

Preferably the means for measuring the electrical potential difference includes means for measuring the electrical potential difference between the first and third electrodes and means for measuring the electrical potential difference between the second and third electrodes.

Alternatively, the means for measuring the electrical potential difference includes means for measuring the electrical potential difference between the first and second electrodes and means for measuring the electrical potential difference between the first electrode and the third electrode.

In yet another alternative, the means for measuring the electrical potential difference includes means for measuring the electrical potential difference between the first and second electrodes and means for measuring the electrical potential difference between the second and third electrodes.

In one embodiment of the second aspect of the invention, the sensor includes a first elongate tube having solid electrolyte present at one end thereof, the first electrode being located on an outer face of the solid electrolyte and the second electrode located on an inner surface of the solid electrolyte, a second elongate tube located within the first elongate tube, the second elongate tube having solid electrolyte present at one end thereof, the third electrode being located at an inner surface of the solid electrolyte present at the one end of the second elongate tube, solid electrolyte extending between the second electrode and the third electrode, and the second gas pathway means includes one or more apertures in a side wall of the first elongate tube.

In this embodiment, combustion gas can pass through the one or more apertures in the side wall of the first elongate tube and move through the annular space defined by the outer wall of the second elongate tube and the inner wall of the first elongate tube to reach the second electrode. The second gas pathway means can be seen to include the apertures and the annular space. The oxidation catalyst may be provided in the second gas pathway means by coating one or both of the outer wall of the second elongate tube or the inner wall of the first elongate tube with the oxidation catalyst. This is especially effective in cases where the distance between the inner wall of the first elongate tube and the outer wall of the second elongate tube is small, thereby ensuring that combustion gas travelling along the annular space contacts, or comes into close proximity with, the oxidation catalyst. Alternatively, the catalyst may be provided by locating a gauze of catalyst or particles of catalyst in the annular space or by otherwise locating the catalyst in the annular space.

The means to measure the electrical potential differences may include one or more electrical leads separately connected to each of the first, second and third electrodes. These electrical connections may be similar to those described in respect of the first aspect of the invention and will not be described further.

In use of the sensor of the second aspect of the invention, the sensor is placed in a combustion gas stream. The combustion gas contacts the first electrode. The second electrode is contacted by combustion gas that has been brought into equilibrium by contact with the oxidation catalyst. The third electrode is contacted by reference gas of known oxygen concentration. Due to the differences in oxygen partial pressure of the gas contacting each respective electrode, electrical potential differences are established between the first and second electrodes and the first and third electrodes. Measurement of the electrical potential difference between the first and third electrodes enables the oxygen concentration of the combustion gas to be calculated. Similarly, measurement of the electrical potential difference between the second and third electrodes enables the oxygen concentration of the oxidised (or equilibrated) combustion gas to be measured. The difference in the oxygen concentrations between the raw combustion gas and the equilibrated combustion gas allows the concentration of unburnt fuel in the combustion gas to be determined. The difference in oxygen concentration between the equilibrium and non-equilibrium gas is due to the presence of unburnt fuel. This unburnt fuel consists mainly of carbon monoxide and hydrogen, which react according to the following equation:

$$CO+H_2+O_2 \rightarrow CO_2+H_2O \qquad (3)$$

Equation (3) can be used to calculate the amount of unburnt fuel present in the combustion gas.

The sensor of the second aspect of the invention allows the simultaneous monitoring of both the oxygen and unburnt fuel concentrations of a combustion gas. The sensor provides a unitary device that requires only a single access port in an exhaust duct or other exhaust gas carrying means. The value of the electrical potential difference across the solid electrolyte is dependent upon the temperature of the electrolyte. Therefore, the sensor should incorporate a thermocouple or other temperature measuring means to measure the temperature of the solid electrolyte. Any known thermocouple may be used. A preferred construction includes two wires of dissimilar materials located within the inner tube of the sensor and joined to each other adjacent the solid electrolyte. The two dissimilar wires form the thermocouple, with the hot junction being the above-described junction of the two wires adjacent the solid electrolyte and the cold junction being at a remote location maintained at known temperature.

The sensor of the second aspect of the invention requires only three electrodes. The first and second electrodes are separated by solid electrolyte, as are the second and third electrolytes. The solid electrolyte may constitute a unitary body having the three electrodes formed on appropriate surfaces thereof. Alternatively, the solid electrolyte may comprise two separate pieces of electrolyte, with one piece having two electrodes formed on appropriate surfaces thereof and the other piece having the remaining electrode formed thereon, the other piece of electrolyte being placed in electrical contact with the one piece of electrolyte.

The preferred electrical potential differences measured in the sensor of the second aspect of the invention are the electrical potential differences between the first and third electrodes (which allows the oxygen concentration of the raw combustion gas to be determined) and the second and third electrodes (which allows the oxygen concentration of the equilibrated combustion gas to be determined). This allows oxygen concentrations and the concentration of unburnt combustible gas to be determined.

It is also possible to measure the electrical potential differences between the second and third electrodes, (which enables the oxygen concentration of the equilibrated combustion gas to be determined) and between the first and second electrodes (which allows the difference in oxygen concentration between the raw combustion gas and the equilibrated combustion gas to be determined). Once the oxygen concentration of the raw combustion gas has been determined, the oxygen concentration in the catalysed combustion gas and the concentration of combustible gas in the uncatalysed combustion gas can then be determined.

It is also possible to measure the electrical potential differences between the second and third electrodes, and between the first and second electrodes (which allows the difference in oxygen concentration between the raw combustion gas and the equilibrated combustion gas to be determined). Once the oxygen concentration of the equilibrated combustion gas has been determined, the oxygen concentration of the raw combustion gas and the unburnt fuel concentration of the raw combustion gas can then be determined.

The sensor of the invention may also be constructed such that two pairs of electrodes are used, with each electrode of a pair being separated by solid electrolyte. In this construction, the solid electrolyte of one pair of electrodes does not necessarily have to be in electrical contact with the solid electrolyte of the other pair of electrodes.

Accordingly, in a third aspect, the present invention provides a sensor for determining oxygen and/or unburnt fuel content of a combustion gas comprising a first solid electrolyte having a pair of electrodes located on generally opposite surfaces thereof, a second solid electrolyte having a pair of electrodes located on generally opposite surfaces thereof, wherein in use a reference gas of known oxygen concentration is supplied to at least one of said electrodes, and a combustion gas is supplied to at least one of said electrodes, and an equilibrated combustion gas is supplied via a gas pathway means to at least one other of said electrodes, said gas pathway means arranged such that combustion gas flows therealong and contacts or comes into close proximity with an oxidation catalyst before contacting its respective at least one of said electrodes, means to measure an electrical potential difference between the pair of electrodes on the first solid electrolyte, means to measure an electrical potential difference between the pair of electrodes on the second solid electrolyte, wherein one of said reference gas, combustion gas or equilibrated combustion gas contacts one electrode of each pair of electrodes on the first solid electrolyte and the second solid electrolyte.

Preferably, the equilibrated combustion gas contacts one electrode of each pair of electrodes.

In a preferred embodiment of the third aspect of the invention, the first solid electrolyte is mounted in or forms part of a first tube and the second solid electrolyte is mounted in or forms part of a second tube, said second tube being located within said first tube. In this embodiment, it is advantageous to supply the reference gas through a bore or passage inside the second tube and to allow the combustion gas to contact the electrode that is located on the outside of the first tube. The annular space located between the inner wall of the first tube and the outer wall of the second tube provides the gas pathway means for supplying equilibrated combustion gas to the inner electrode of the first tube and the outer electrode of the second tube. The annular space is provided with an oxidation catalyst in the same manner as described for the second aspect of the invention.

In all of the aspects of the invention, it is necessary that the gas contacting at least one of the sensors is an equilibrated combustion gas and the invention allows this to be attained by passing the combustion gas along a gas pathway means that includes an oxidation catalyst. The gas pathway must be sufficiently long in relation to its width to ensure that the time of contact between the gas and the catalyst is long enough to cause the gas to essentially reach equilibrium before contacting the relevant electrode.

DETAILED DESCRIPTION OF THE INVENTION

Figures 1, 2, 3, 4:
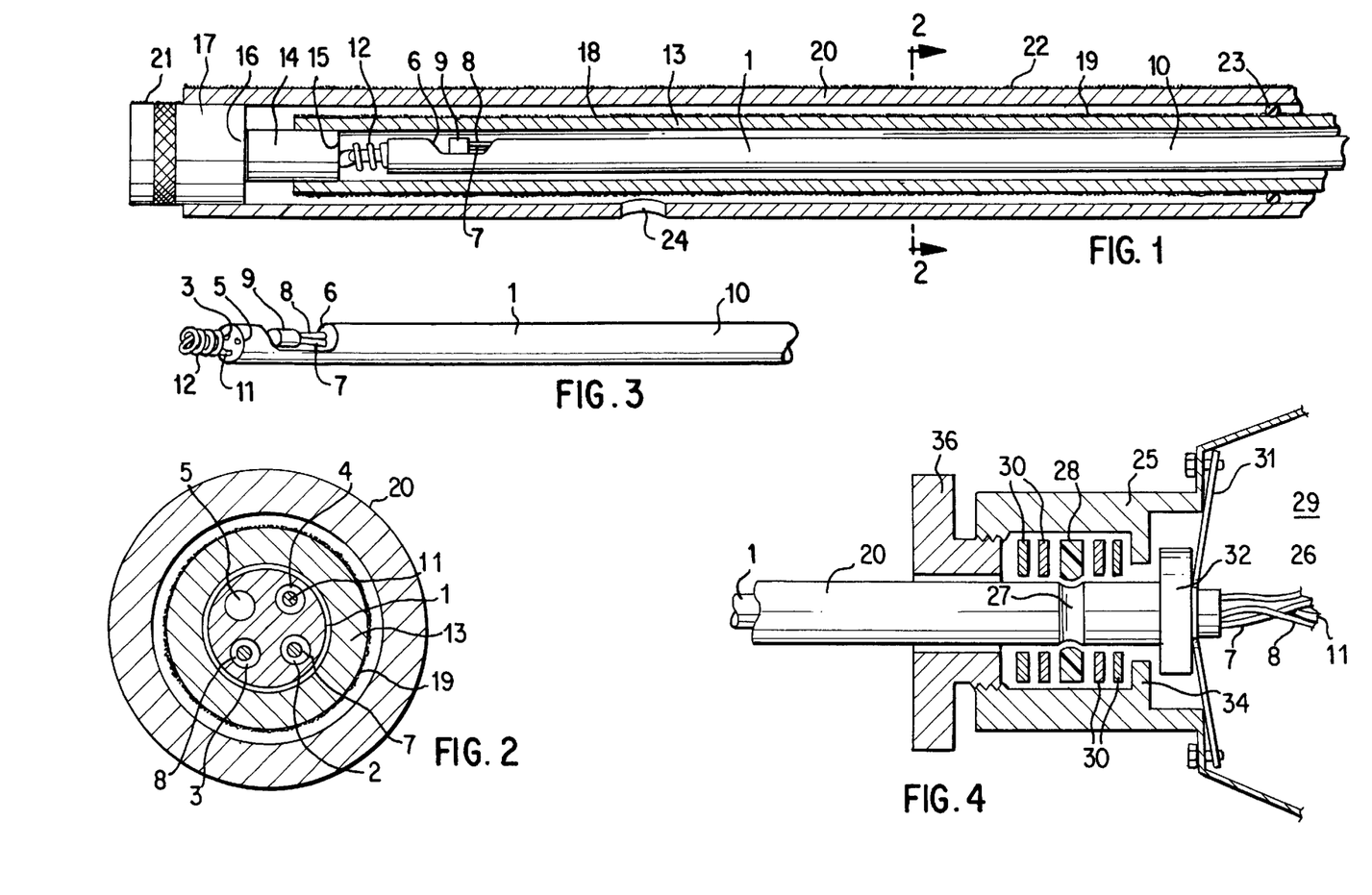
FIG. 1 is a side view of one end portion of the one embodiment of a sensor in accordance with the second embodiment of the invention shown in sectional view.
FIG. 2 is a cross-sectional view taken along line A—A in FIG. 1.
FIG. 3 is a perspective view of one end portion of an inner tube of one embodiment of a sensor in accordance with the invention.
FIG. 4 is a side view of the other end portion of one embodiment of a sensor connected to a housing shown in section.

In FIGS. 1 to 3, there is shown an elongate cylindrical inner tube or rod 1 having four bores 2, 3, 4, 5 extending lengthwise through the rod. The rod 1 forms part of a first embodiment of the sensor. Three of bores 2, 3, 4 are provided to house wires which, in use, extend through the bores. The other bore 5 provides a passageway for a reference oxygen atmosphere (to be described later). The rod 1 typically has a diameter of about 4.0 to 4.5 mm with each of the four bores being typically 0.5 to 1.5 mm in diameter. Typically, the rod is composed of 99.7% alumina. However, the composition of rod 1 may comprise any other suitable non-electrically conductive material.

A notch 6, which is located towards one end of rod 1, is of a depth sufficient to cut through bores 2, 3 whilst maintaining bores 4, 5 intact. Advantageously, notch 6 extends about halfway through the diameter of rod 1.

Wires 7,8 extend through bores 2,3, respectively and the free ends of these wires extend into notch 6 where they are joined together by clip 9. Wires 7,8 are of dissimilar material and are in electrical connection to form the hot junction of a thermocouple used to measure the temperature of the atmosphere into which the sensor is inserted. End portion 10 of the rod is referred to as the cool or cold end and is contained in a sensor housing (to be described later) which is located outside the unit.

In the sensor shown in FIGS. 1–3, rod 1 has an outside diameter of 3 mm. Each of bores 2,3,4,5 has an inner diameter of 0.85 mm. Tube 13 has an inner diameter of 3.5 mm and an outer diameter of 4.5 mm. Tube 20 has an inner diameter of 5 mm and an outer diameter of 8 mm.

Wire 11 which extends through bore 4 projects outwardly from the end of rod 1 and is formed into a spiral spring arrangement 12 at the end of rod 1. The free end of wire 11 is folded back upon itself to be received in the end of bore 4 in order to securely locate and maintain spiral spring arrangement 12. Wire 11 forms one common part of both electrical circuits of the sensor. One circuit may be referred to as the oxygen detection circuit, the other may be referred to as the unburnt fuel detection circuit. Preferably, wire 11 should be made from platinum.

Rod 1 is located in a support internal tube 13 as shown in FIG. 1. Typically, this tube is composed of up to about 99.9% alumina, but may comprise any other suitable non-electrically conductive material. Tube 13 is sealed at one end by pellet (or disk) 14 of oxygen sensitive material (solid electrolyte). Advantageously pellet 14 comprises stabilised zirconia and is coated with a Pt coating on both sides to form electrodes 15 and 16. Electrode 15 is in contact with spring arrangement 12 and electrode 16 is in contact with another pellet (or disk) 17 of oxygen sensitive material (solid electrolyte). Advantageously pellet 17 is also composed of stabilised zirconia. The external surface of the tube 13 is coated by a catalytic active material 18. Alternately, the internal surface of tube 20 may be coated by the catalytic active material 18, or both surfaces may be so coated. In still another embodiment, a gauze of catalyst or particles of catalyst may be disposed within the annular space between tubes 13 and 20. Preferably the catalytic material comprises platinum and extends from the end of tube 13 for a distance of 10–120 mm, preferably 14 mm. Current conductor 19 formed from Pt paste, provides an electrical path from pellet 14 to the other end of the sensor. It is advantageous that there be two such electrical paths from the end of the sensor, joining through the catalyst, so that the catalyst can be tested. This may be done by measuring the electrical resistance from one of the electrical paths to the other. If this electrical resistance increases beyond a certain limit, it may indicate that the catalyst has deteriorated and may be ineffective.

Tube 13 is located inside outer tube 20 as shown in FIG. 1. Typically, this tube is composed of up to about 99.9% alumina, but it may comprise any other suitable non-electrically conductive material.

Tube 20 is sealed at one end by pellet (or disc) 17 of oxygen sensitive material (solid electrolyte). Advantageously pellet 17 is composed of stabilised zirconia and is coated with Pt on both sides to form electrodes. The external side of pellet 17 has electrode 21 formed thereon and this electrode, in use, contacts the combustion gas directly inside of the furnace of kiln. The internal side of pellet 17 is electrically connected to electrode 16 of pellet 14. Preferably, the material of the electrode 16 of pellet 17 is also Pt. Current conductor 22 is formed from Pt paste to provide an electrical path from pellet 17 to the cool end of the probe. Typically, conductors 19,22 have an identical composition to that of wire 11 as described above. The gap between tube 13 and tube 20 is sealed at the cool end of the probe by ring 23 of a glass material.

Wires 7,8 forming the thermocouple are completely separate from wire 11, measuring electrode 16 and current conductor 19 (which form a circuit for unburnt fuel detection). With this arrangement wires 7,8 may be selected to provide the optimum performance for measuring the temperature by thermocouple. Wire 11, measuring electrode 21 and current conductor 22 form the oxygen detection circuit. Current conductor 22, and consequently wire 11, which may not be of identical composition to current conductor 22, may be selected to provide optimum corrosion-resistance in the corrosive atmosphere of some furnaces. Apertures 24 in external tube 20 allow combustion gas to enter the annular space between tubes 13 and 20 and provide a pathway for supplying the gas to electrode 16. The apertures 24 are made in the body of tube 20 a distance of about 100–120 mm from the end of tube 13, just opposite of the end of catalytic active material.

Bore 5 provides a pathway for the reference oxygen atmosphere which is typically 20.9% oxygen to be admitted from outside the sensor to surround the internal side of the pellet 14. The exposed portion of pellet 14 with electrode 16 is in contact with equilibrated combustion gas which has passed through apertures 24 and contacted the catalyst material. The difference in electrical potential in the circuit comprising wire 11, spring arrangement 12, electrode 21 of pellet 17 and current conductor 22 corresponds to the oxygen content of the combustion gas. In use, an electrical potential difference is produced between the ends of the oxygen sensitive pellet 14 which may be used to determine the oxygen concentration of the equilibrated combustion gas. This, in turn, may be used to determine the excess of oxygen and additionally the unburnt fuel contents of the furnace, boiler or kiln (calculated as carbon monoxide) atmosphere, following oxidation to carbon dioxide according to Equation ③ on the catalytic active material 18 in the presence of excess oxygen. As a result, the sensor can simultaneously measure oxygen and unburnt fuel concentration in the combustion gas.

Turning now to FIG. 4, which discloses details of the connection of support tube 20 to housing 25 of the sensor, there is shown the other end portion of tube 20 to that shown in FIGS. 1–3. The end portion shown in FIG. 4 may be referred to as the cold or cool end portion as it is not inside the furnace boiler or kiln's atmosphere, but rather inside the housing 25 of the probe connected to the outside of the unit. Wires 7, 8, 11 and current conductors 19,22 are shown extending from the cool end portion of tube 20. Plastic conduit 26 which is connected to the bore 5 is used to admit the reference oxygen atmosphere to rod 1. A groove 27 which is located towards the adjacent end of tube 20 is provided with a close-fitting neoprene rubber grommet 28 so that tube 20 may be sealed to housing 25 in order that no furnace atmosphere may leak into the housing interior 29. Additionally, grommet 28 acts as a cushion during transportation and use of the sensor which enhances the reliability of the sensor. Two metal washers 30 are located on both sides of rubber grommet 28 on tube 20 to facilitate sealing the tube to the housing and to prevent escape of the furnace atmosphere into the interior of the efficiency probe. Grommet 28 provides a buffer for the contact of the metal washers to the ceramic material of the rod 1. A leaf spring 31 which is fixedly attached to the housing 25 of the sensor is biased in the direction of the hot end of the tube to bear against a nylon collar 32. Nylon collar 32 is fixedly connected to the cool end of the rod 1 and is rigid towards or pressed against the cool end of tube 20 by means of spring 33. Flange 34 of housing 25 provides an abutment surface for the adjacent metal washer 30, the washers 30 being received spring and on the support tube 20 in an extension 35 of the housing which is threaded at its free end to threadably receive a threaded member 36 inside the extension 35. Upon rotation of member 36, the washers 30 and grommet 28 are gradually tightened together until the washer nearest the flange contacts the flange and the tube is securely sealed to the housing. In this condition, the nylon collar 32 remains spaced from the flange 34 so as to maintain the biasing effect of the leaf spring 33 by which the spring arrangement 12 is maintained in contact with the pellet 14.

The described arrangement of fixing the tube 20 to the housing 25 allows for flexibility of the tube yet provides a tight seal to protect the interior of the housing.

A hollow cylindrical protecting tube (not shown in FIGS. 1 to 4) may be fitted to the housing over tube 20 in order to protect tube 20 by covering it. The annular space between the inside of the protecting tube and the outside of tube 20 may be filled with a heat resistant material. This material further enhances the temperature shock resistance of the sensor and also improves the physical shock resistance to a large degree, particularly during insertion into and withdrawal from very hot environments. The furnace atmosphere must still be accessible to the exposed portion of the pellet 17 and the pellet 17 may project from the protection tube or the protection tube may have one or more openings therethrough to enable the measuring atmosphere to permeate through the filling material.

One advantage of the above described embodiment is that there is no spring pressure on the hot junction 9 of the thermocouple but rather the hot junction is located in notch 6 which affords protection for the hot junction against thermal and physical shock. This makes the probe more robust and reliable in use. The hot junction 9 measures the temperature of the pellets 14,17 and the temperature of the measuring atmosphere when the hot end id disposed in the unit atmosphere.

The described arrangement has been advanced merely by way of explanation and many modifications may be made thereto.

Figure 5A:
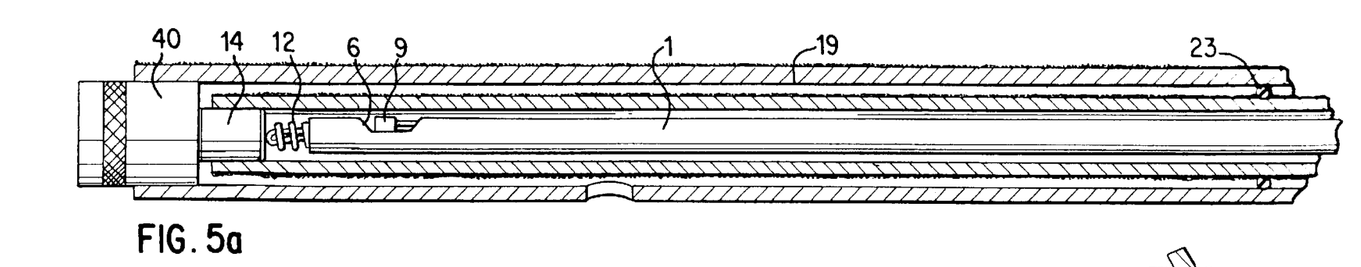
FIG. 5a is a view similar to FIG. 1 with another design of a zirconia/alumina cell as part of a second embodiment of the sensor of the invention.
Figures 5B, 6:
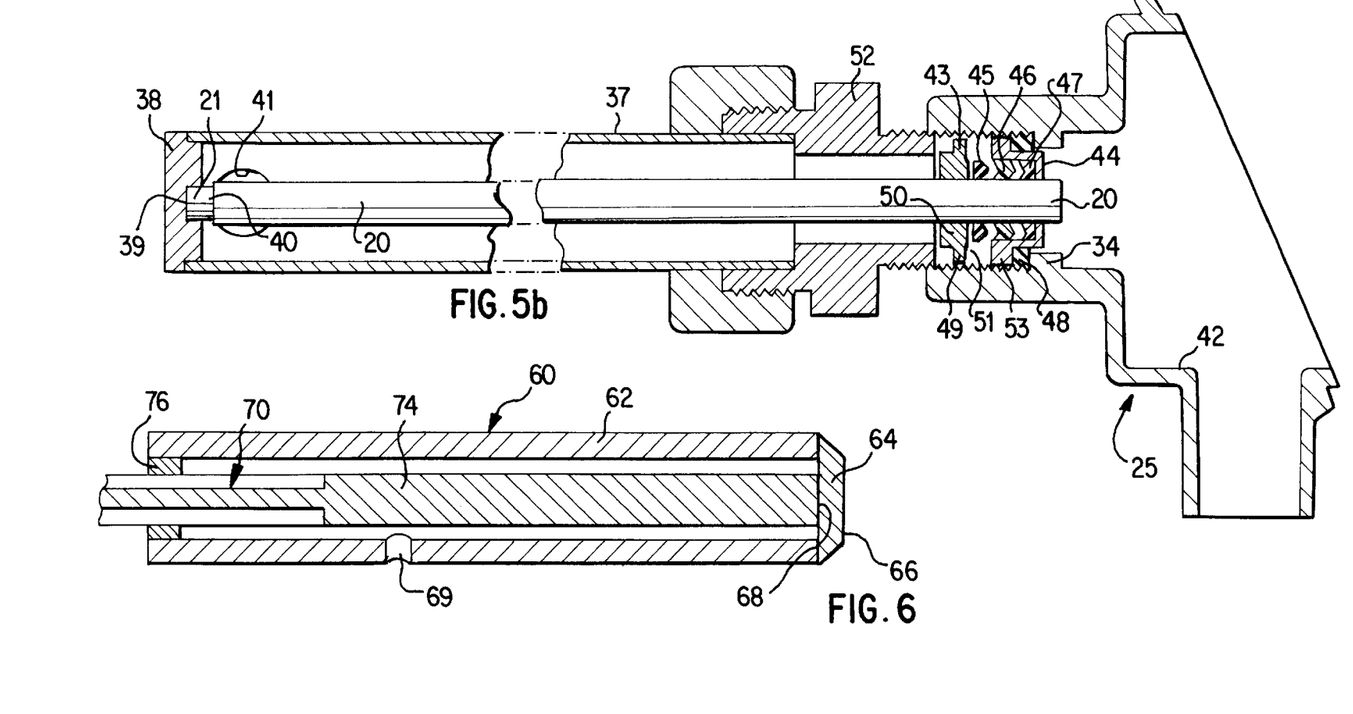
FIG. 5b is a side view partly in section of the embodiments of the sensor.
FIG. 6 shows a sensor in accordance with another embodiment of the present invention.

One of such modifications is shown in FIGS. 5a and 5b. In this embodiment, a metal outer protecting tube 37 is closed at its distal or hot end (which protrudes into the furnace) by a metal plug 38 which is connected to tube 37 by any suitable means such as welding. A recess 39 is centrally located in the internal surface of plug 38 to receiving the measuring electrode 21 of pellet 17. The above-mentioned combination of pellets 14 and 17 could be manufactured as one monolithic pellet 40. The walls of recess 39 are of slightly larger diameter in the direction from the internal surface of the plug. Typically, the diameter of the recess at the internal surface is 1 mm less than the diameter of the base of the recess. Thus, pellet 40 and, accordingly, tube 20 are securely held in place. Outer tube 37 is provided with ports 41 (only one shown) in its wall to allow the measuring environment to surround tube 20 and pellet 40. Outer tube 37 and plug 38 are both electrically conductive and become part of the oxygen detection circuit when suitable connection is made inside the head 42 of the housing 25, thereby replacing external current conductor 22 of the previously described embodiment. As the outer tube 37 may be manufactured from rugged materials, there is less chance that it will be corroded or damaged in the unit.

FIG. 5b also illustrates another modification, this time in the sealing of tube 20 to head 42 of housing 25 and pellet 40. The embodiment described below is an alternative embodiment to that described earlier for the corresponding features of sealing and pellet 40. FIG. 5b illustrates the sensor when in a loosely secured configuration, prior to being fully tightened. The tube 20 is sealed to head 42 by an arrangement including two metal washers 43,44 typically made of brass or similar material, three sealing rings 45,46,47 of complementary shape, typically made of teflon or similar material, and a flexible "O"-ring 48, typically made of neoprene or similar material. Washer 43, which is located towards the hot end of the probe in tube 20 has a central portion 49 of relatively larger diameter, an end portion 50 of intermediate diameter, which in use is located towards the hot end of the sensor, and a shoulder portion 51 of relatively smaller diameter which in use is located towards the cool end. Shoulder portion 51 provides positive location of the three sealing rings, both in intimate contact with each other and against washer 44, when nut 52 is tightly screwed to head 42. Sealing rings 45,46 are provided with a single sealing surface, and sealing ring 47 is provided with two sealing surfaces, such that two adjacent sealing surfaces are of complementary shape and fit together intimately when in tightened together. A typical set of complementary shapes are shown in FIG. 5b having matching circular troughs and ridges which matingly engage. Washer 44 is substantially cup-shaped and located on the cool end of tube 20 with the base of the cup towards the cool end so that the three sealing rings are between the two washers, and are received in the cup of washer 43. The rim of the cup of washer 43 is provided with a flange 53 so that O-ring 48 is squeezed between flange 53 and flange 34 provided on head 42 (as described previously). In this embodiment the cool end of the tube 20 is located inside nylon collar 32 and connected to the head 42 by way of leaf spring 31 as described previously and illustrated in FIG. 4.

Another embodiment of the present invention is shown in FIG. 6. The sensor 60 of FIG. 6 is capable of detecting a non-equilibrium mixture in a combustion gas, but cannot measure oxygen content. The sensor 60 includes a hollow alumina tube 62 sealed at one end by a pellet of solid electrolyte 64. Electrodes 66,68 are located on the outer face and inner face, respectively, of solid electrolyte 64. A solid alumina rod 70 is mounted within hollow tube 62 and a coating of platinum catalyst 74 is applied to the surface thereof. The coating of platinum catalyst extends at least from the solid electrolyte to adjacent one or more apertures 69 formed in hollow tube 62. The end of hollow tube 62 distant from the solid electrolyte is sealed by a gas tight sealing means 76. Electrical connecting means (not shown) enable the emf between electrodes 66,68 to be measured.

In use, sensor 60 is placed in a combustion gas stream. Raw combustion gas contacts outer electrode 66. Combustion gas also passes through one or more apertures 69 and diffuses along the annular space provided between the outer surface of rod 70 and the inner surface of hollow tube 62. The platinum catalyst 74 acts to oxidise any carbon monoxide and other products of incomplete reaction (if excess oxygen is present) and thus the combustion gas contacting inner sensor 68 is substantially in equilibrium. The difference in oxygen concentrations of the gases contacting the inner and outer electrodes causes a Nernst emf to be generated and the presence of this signal means that incomplete combustion or non-equilibrium conditions are present. The magnitude of this signal also enables the unburnt fuel concentration (calculated as monoxide concentration) to be calculated in accordance with equation ③.

Figure 7:
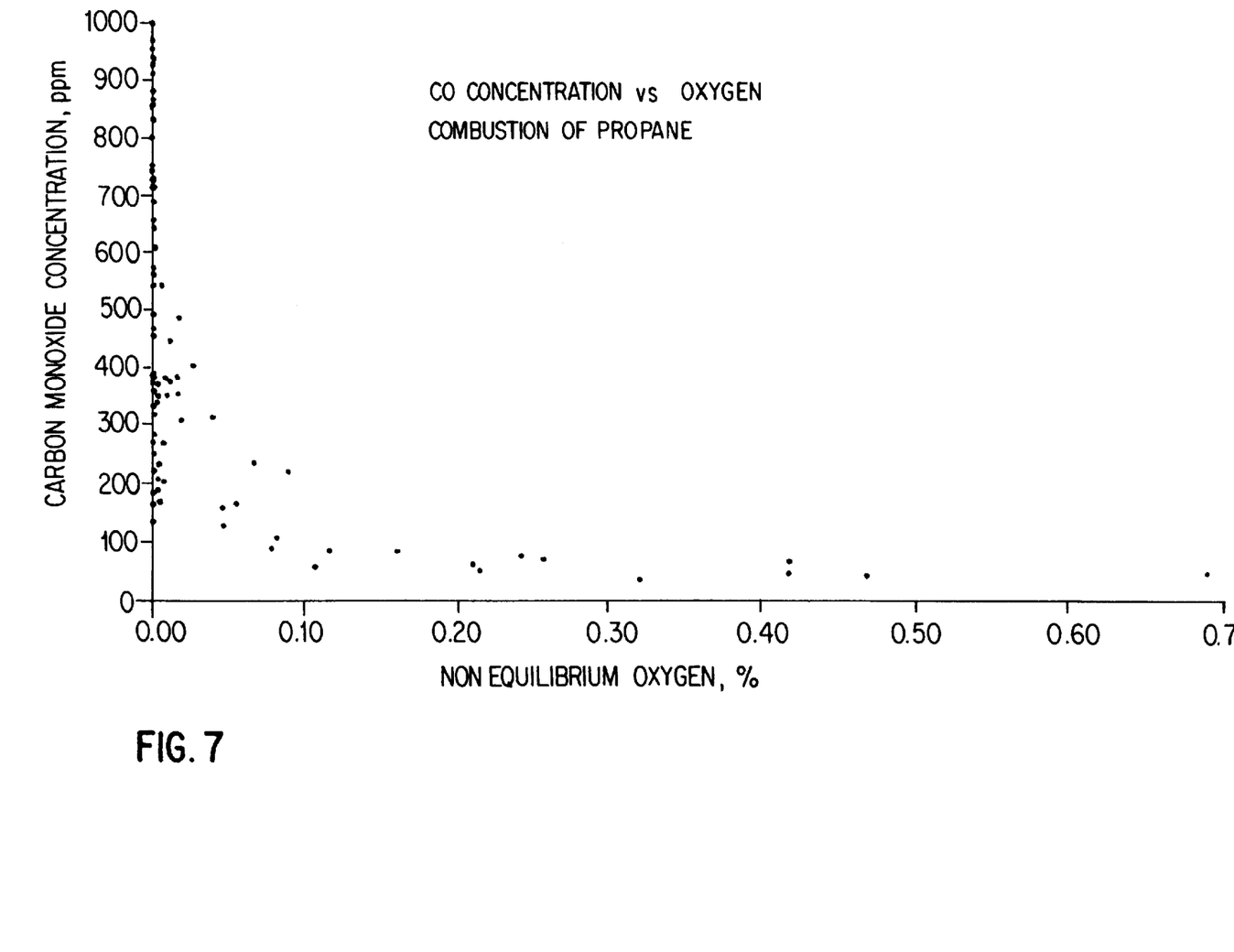
FIG. 7 shows a plot of carbon monoxide content, as measured by a proprietary carbon monoxide measuring means, plotted against oxygen concentration in a flue gas.

A series of tests were conducted to show the working of the sensor of the present invention. In the first test, a conventional single sensor was used to measure the oxygen content of a combustion or flue gas. At the same time, the concentration of carbon monoxide was measured by a proprietary carbon monoxide concentration measuring means. The results showing both the carbon monoxide concentration and the emf difference between the electrodes of the conventional sensor (which indicates oxygen concentration) are shown in FIG. 7. This Figure shows that it is still possible to have significant levels of carbon monoxide (up to 100 ppm) even with 1% oxygen in the flue gas.

Figure 8:
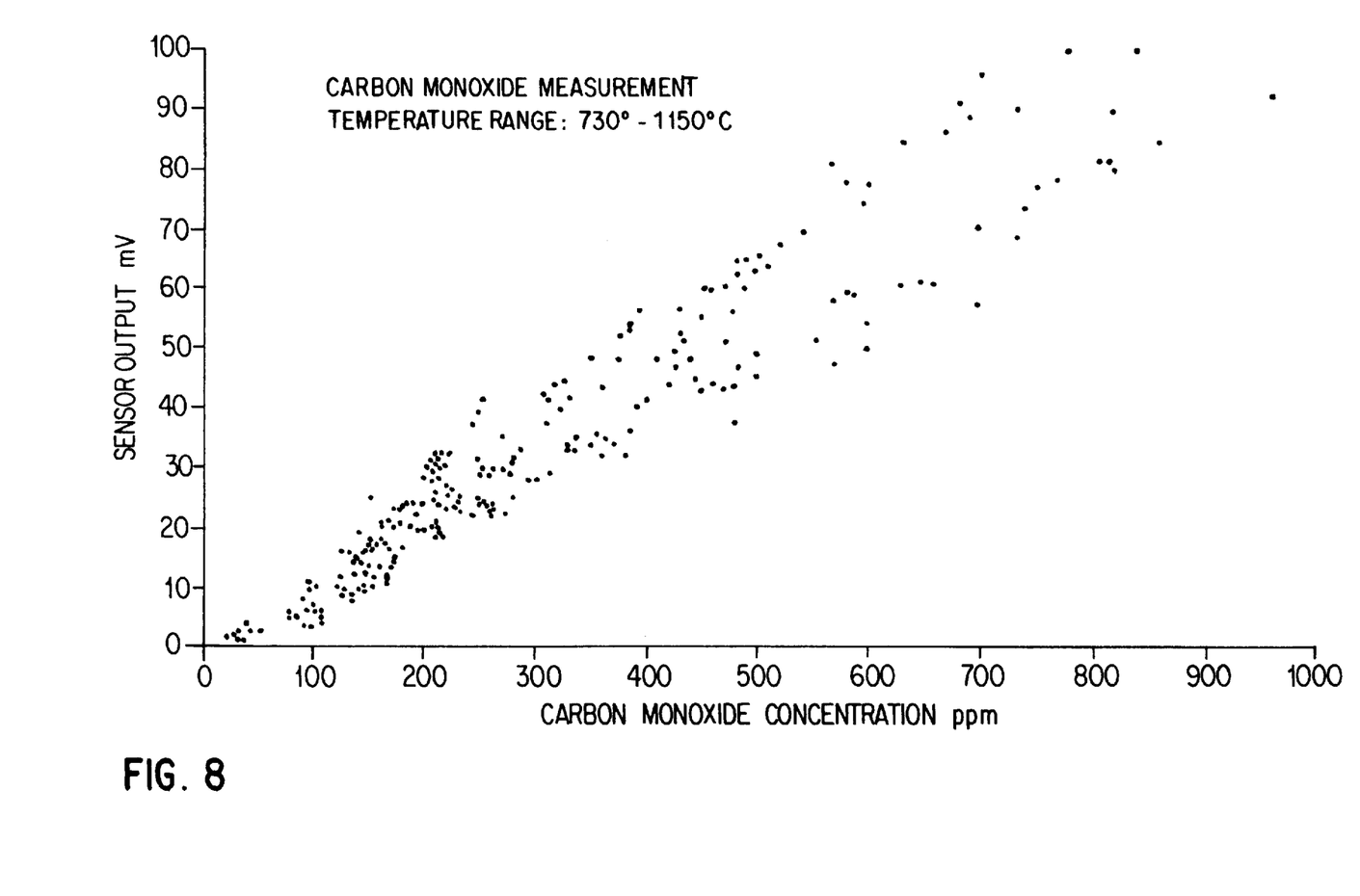
FIG. 8 shows a plot of emf difference against CO concentration using a sensor in accordance with the present invention.

FIG. 8 shows a plot of the emf difference developed between the inner and outer sensor as a function of the carbon monoxide concentration. The plot in FIG. 8 was obtained using a sensor as shown in FIG. 1.

If it is assumed that the mixing of fuel and air is imperfect for small amounts, say 0.01%, of excess air and almost complete for larger amounts, say 10%, of excess air, then this straight line can be predicted from basic chemical stoichiometry.

This relationship applies for carbon monoxide concentrations in the range 0 to 1000 ppm. Beyond this, the sensor saturates and there is no further change in the output. It is postulated that beyond 1000 ppm of carbon monoxide, there is so little oxygen available that no further combustion of the gas is possible, even in the presence of a catalyst.

The sensor of the present invention can detect and measure the products of incomplete combustion, notably carbon monoxide. It does so by measuring separately the oxygen that remains from the use of excess air and the oxygen that remains from incomplete combustion.

This sensor can therefore be used to measure the efficiency of the combustion. It can also be used to provide safe reliable control of fuel air ratio, because incomplete combustion or imperfect mixing can be detected directly.

It will be appreciated that the invention described herein is susceptible to variations and modifications other than those specifically described. It is to be understood that the invention encompasses all such variations and modifications that fall within the spirit and scope of the claims.

What is claimed is:

1. A sensor for measuring oxygen and unburnt fuel content of a combustion gas, said sensor comprising:
   a first electrode configured to make contact with said combustion gas;
   a second electrode;
   a third electrode;
   solid electrolyte, disposed between each of said first, second, and third electrodes;
   a first gas pathway for passing a reference gas of known oxygen concentration to said third electrode;
   a second gas pathway for passing said combustion gas to said second electrode;
   an oxidation catalyst disposed within said second gas pathway and within close proximity of said combustion gas in said second gas pathway; and
   a measurement device for measuring electrical potential difference between pairs of electrodes, said pairs including at least two pairs selected from a list consisting of:
   a) the first and second electrodes;
   b) the first and third electrodes; and
   c) the second and third electrodes.

2. The sensor of claim 1 wherein said at least two pairs includes said first and third electrodes and said second and third electrodes.

3. The sensor of claim 1 wherein said at least two pairs includes said first and second electrodes and said first and third electrodes.

4. The sensor of claim 1 wherein said at least two pairs includes said first and second electrodes and said second and third electrodes.

* * * * *